United States Patent [19]

Suga

[11] Patent Number: 5,301,154

[45] Date of Patent: Apr. 5, 1994

[54] TIME CALCULATING DEVICE

[75] Inventor: Fusao Suga, Akishima, Japan

[73] Assignee: Casio Computer Co., Ltd., Tokyo, Japan

[21] Appl. No.: 80,226

[22] Filed: Jun. 21, 1993

[30] Foreign Application Priority Data

Jul. 16, 1992 [JP] Japan .................... 4-212049

[51] Int. Cl.$^5$ .................... G04B 47/00; A61B 5/04; A61B 5/02
[52] U.S. Cl. .................... 368/10; 368/107; 128/670; 128/690; 128/707; 364/569
[58] Field of Search .................... 368/10, 11, 107-113; 128/668, 669, 670, 687-690, 706, 707; 364/569

[56] References Cited

U.S. PATENT DOCUMENTS

| | | |
|---|---|---|
| 4,281,663 | 8/1981 | Pringle . |
| 4,305,401 | 12/1981 | Reissmueller et al. . |
| 4,312,358 | 1/1982 | Barney .................... 128/670 |
| 4,367,752 | 1/1983 | Jimenez et al. .................... 128/689 |
| 4,566,461 | 1/1986 | Lubell et al. . |
| 4,770,528 | 12/1988 | Nakao et al. .................... 272/73 |
| 4,807,639 | 2/1989 | Shimizu et al. . |
| 4,998,725 | 3/1991 | Watterson et al. .................... 128/25 |
| 5,067,710 | 11/1991 | Watterson et al. .................... 272/129 |
| 5,158,093 | 10/1992 | Shuartz et al. .................... 128/707 |

Primary Examiner—Vit W. Miska
Attorney, Agent, or Firm—Frishauf, Holtz, Goodman & Woodward

[57] ABSTRACT

A time calculating device calculates a time which a user of the device requires to run a distance such as a whole distance of a marathon race. The time calculating device is provided with a pulse frequency memory which measures pulse frequencies of the user when the user runs a given distance at least twice at predetermined different paces, and which stores the measured pulse frequencies. The time calculating device is further provided with an age input key for inputting age data of the user, and a distance input key for inputting a distance. A running speed at which the user of an age can keep running continuously is calculated from the pulse frequencies stored in the pulse frequency memory and age data input by the age input key. Further, a time is calculated which the user requires to run the distance inputted by the distance input key at the calculated running speed. The calculated time is displayed on a display unit of the time calculating device.

17 Claims, 8 Drawing Sheets

TIME CALCULATING DEVICE

BACKGROUND OF THE INVENTION

1. Field of the Invention

The present invention relates to a time calculating device which is capable of calculating a time that a user will need to finish a certain quantity of exercise.

2. Description of the Related Art

An apparatus is known that counts and displays a pulse frequency of a person to examine physical condition of the person. Such an apparatus is disclosed in U.S. Pat. Nos. 4,305,401, 4,281,663 and 4,566,461. Further, the above apparatus is described in U.S. Pat. No. 4,807,639, U.S. Ser. No. 07/680,239 filed on Apr. 3, 1991 and U.S. Ser. No. 08/015,636 filed on Feb. 9, 1993, all of which have been assigned to the same assignee of the present invention.

For example, in U.S. Pat. No. 4,807,639, there is disclosed an apparatus with a stop watch function, which counts a pulse frequency of a person and a time required for the person to finish a certain quantity of exercise to evaluate his (or her) physical strength. With the apparatus, however, physical strength of the person can be obtained when he has finished exercise, but data can not be obtained before he starts exercise or while he is taking exercise, the data which represents how much of time the user will need to finish exercise of predetermined hardness.

SUMMARY OF THE INVENTION

The present invention has an object to provide a time calculating device which is capable of calculating a time which a user will require for finishing a predetermined quantity of exercise.

According to one aspect of the present invention, there is provided a time calculating device which comprises:

measuring means for measuring data of a living body of a user when the user takes exercise at least twice at different paces;

input means for inputting data of quantity of exercise;

storing means for storing data of exercise quantity inputted by said input means;

calculating means for calculating, based on the data of a living body measured by said measuring means, an estimated time required for finishing exercise quantity expressed by the data of exercise quantity stored in said storing means; and output means for outputting the estimated time calculated by said calculating means.

With the above structure of the time calculating device of the present invention, it can be easily obtained how much time the user will consume to finish a predetermined quantity of exercise.

The other objects and features of the present invention will become understood from the following description with reference to the accompanying drawings.

DETAILED DESCRIPTION OF PREFERRED EMBODIMENTS

Figure 1:
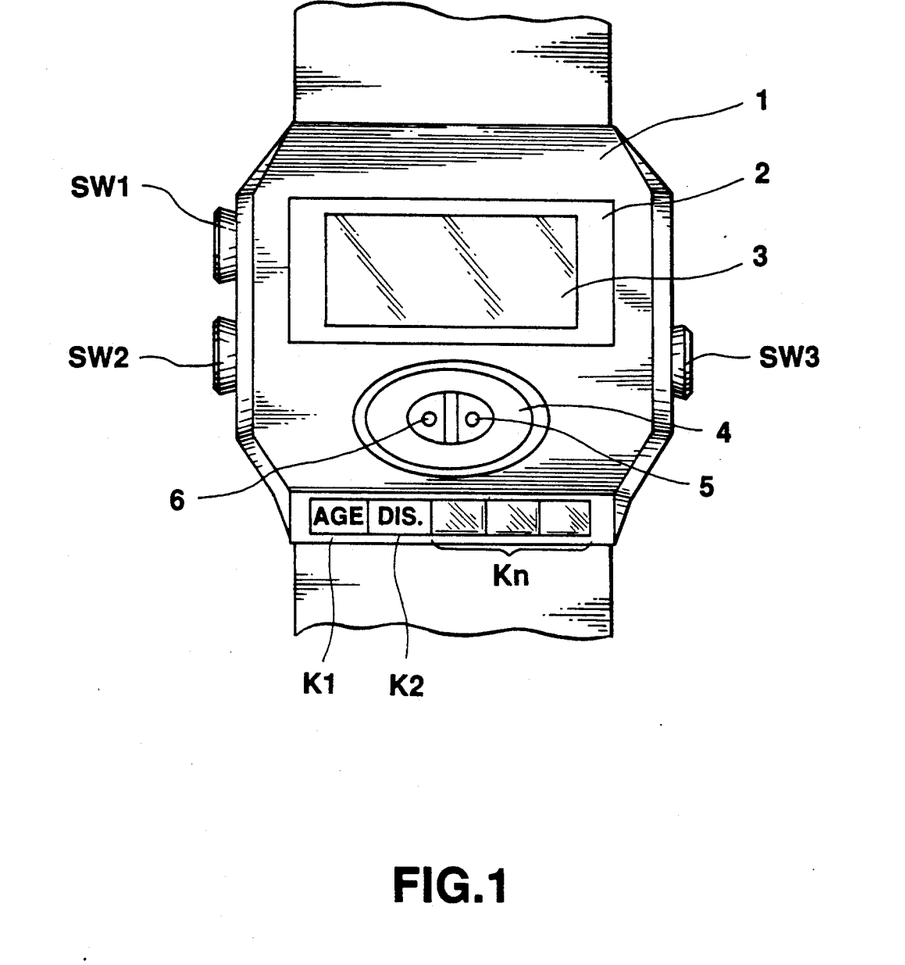
FIG. 1 is a plane view showing an external structure of an electronic wrist watch to which an embodiment of the present invention is applied.

Now, an embodiment of the present invention will be described with reference to the accompanying drawings. The embodiment of the invention is applied to an electronic wrist watch. In FIG. 1, a casing 1 of the wrist watch is provided with a transparent glass 2 on the front surface. A liquid crystal display unit 3 is provided within the transparent glass 2. There is provided a pulse detecting unit 4 at a portion lower to the transparent glass 2 on the casing 1. The pulse detecting unit 4 comprises a light emitting element (a light emitting diode) 5 and a light receiving element (a photo transistor) 6, and serves to optically sense the flow of blood in a finger tip of a user to detect a pulse frequency or a heart rate depending on thickness and thinness of the blood, i.e., depending on thickness and thinness of the hemoglobin in the blood. That is, the light receiving element 6 senses thickness/thinness of the blood, thereby detecting a pulse frequency or a heart rate, when the user puts his finger tip on the pulse detecting unit 4. On a side wall of the casing 1 there are provided switches of a push button type, SW1, SW2 and SW3. Further, there are provided an age input key K1, a distance input key K2 and other keys Kn at a portion lower to the pulse sensing unit 4 on the casing 1.

Figure 2:
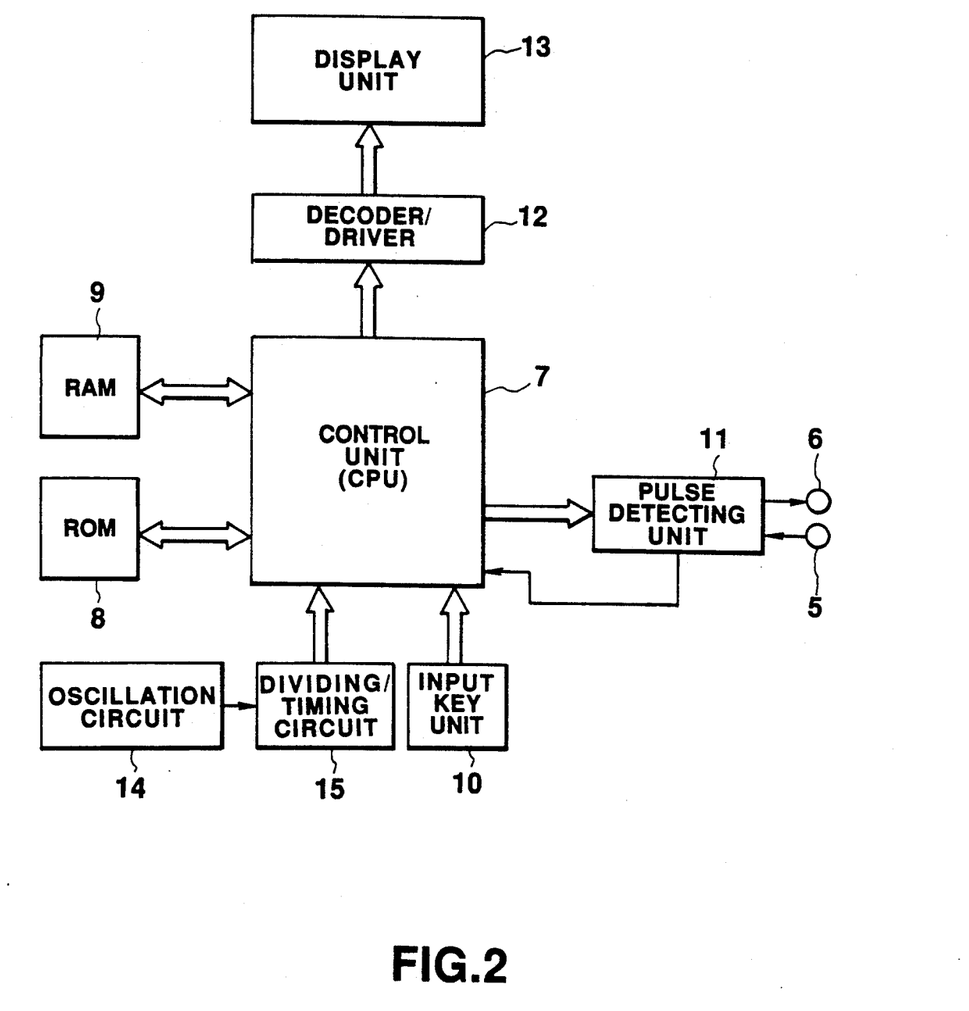
FIG. 2 is a circuit diagram of the electronic wrist watch.

FIG. 2 is a block diagram of circuitry of the electronic wrist watch. A control unit 7 is a central processing unit (CPU) which controls operations of various units connected thereto in accordance with a micro program previously stored in a ROM 8. The CPU 8 performs various processes such as a time calculating process, a pulse frequency measuring process, a predictive running-speed calculating process, a predictive time calculating process. A RAM 9 is a memory which stores various data, as will be described later. An input key unit 10 includes the switches SW1 to SW3 and keys K1 to Kn shown in FIG. 1, and sends a key input signal to the control unit 7 in response to key operation.

The switch SW1 is a start switch which is operated when a runner (the user) starts trial running to be described later, and the switch SW2 is a goal switch which is operated when the runner finishes the trial running. The switch SW3 is a mode selecting switch which is operated to switch an operation mode to a time calculating mode, a goal time preparation mode, or a goal time display mode. The key K1 is an age input key which is operated to input the age of the runner. The key K2 is a distance input key which is operated to input a distance of a trial running and an actual running distance. Other keys Kn are input keys which are operated when the electronic wrist watch works in another operation mode.

A pulse detecting circuit 11 is connected to the light emitting element 5 and the light receiving element 6 of the pulse detecting unit 4 of FIG. 1. Depending on variation in the blood flow in the finger tip of the runner, the pulse detecting circuit 11 senses increase and/or reduction in quantity of light received by the light receiving element 6, thereby detecting pulses of the runner, and sends pulse signals to the control unit 7 in synchronism with the detected pulses. A decoder/driver 12 decodes display decider outputted from the control unit 7, and sends a display driving signal to a display unit 13.

The display unit 13 includes the liquid crystal display unit 3, and is driven by the decoder/driver 12, thereby displaying various data. An oscillation circuit 14 generates a clock signal of a predetermined frequency and sends the clock signal to a dividing/timing circuit 15. The dividing/timing circuit 15 divides the clock signal sent from the oscillation circuit 14 to produce various timing signals such as a time-calculating signal. The timing signals are transferred to the control unit 7.

Figure 3:
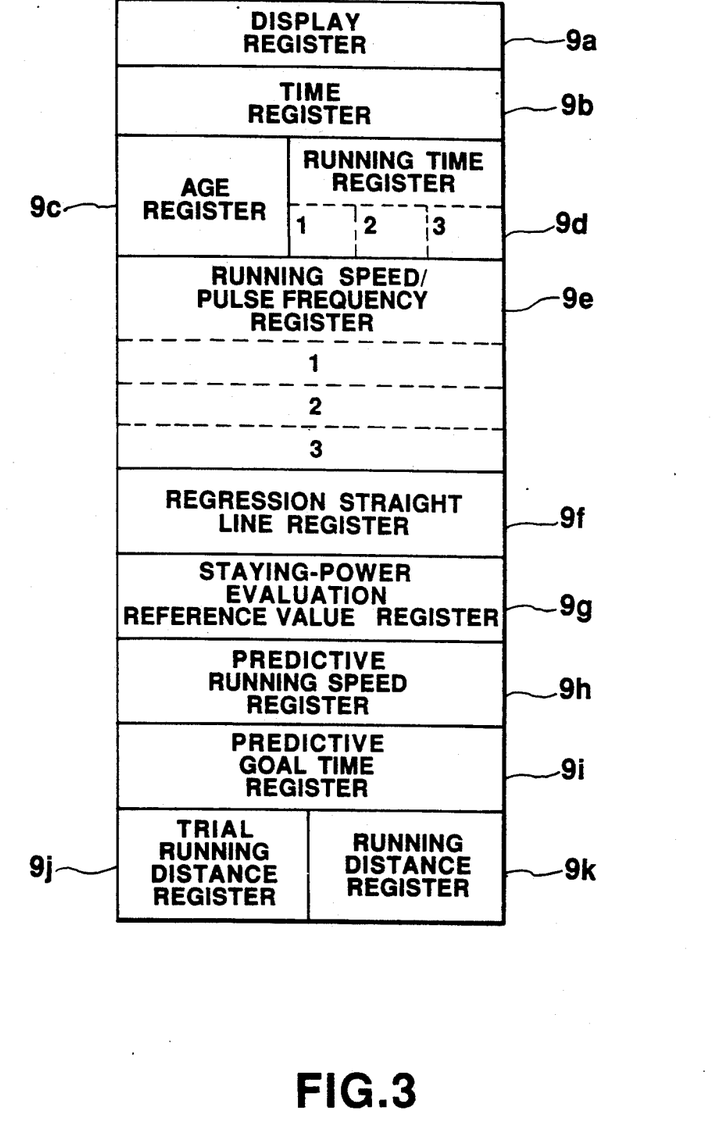
FIG. 3 is a view showing structure of RAM of the embodiment.

FIG. 3 is a view illustrating structure of a memory provided in the RAM 9. A display register 9a stores display data to be displayed on the display unit 13. A time register 9b stores a current time and a current date. An age register 9c stored age data which is input by operation of the age input key K1. The age data is incremented by +1 every time the age input key K1 is operated. A running time register 9d has three memory areas, in which running times defined by operation of the start switch SW1 and operation of the goal switch SW2 in the first to third running are stored, respectively. A running speed/pulse frequency register 9e has memory areas for storing running speeds of the first, second and third trial running and memory areas for storing pulse frequencies or heart rates obtained after the runner has finished the first to third trial running or during the first, second and third running. A speed to be stored in the running speed/pulse frequency register 9e is calculated from time data stored in the running time register 9d and distance data stored in a trial running distance register 9j to be described later. A regression straight line register 9f stores values of constants a and b of a linear equation (a regression straight line): $y = ax + b$.

A staying-power evaluation reference register 9g stores a pulse frequency, i.e., a reference evaluation value of staying power calculated from an expression: $(220 - age) \times 0.75$, where the age is stored in the age register 9c. The reference evaluation value of staying-power represents hardness of exercise which is expressed in terms of a pulse frequency, and means hardness of exercise that a user can keep continuously taking. In other words, the reference evaluation value of staying power is equivalent to 75% of the maximum pulse frequency (maximum heart rate) decided for each age of a user, that is, the maximum pulse frequency, higher than which the pulse frequency of the user of an age can not raise even if the user of the age takes any harder exercise, is expressed by "220 − age", and the reference evaluation value of the staying power corresponds to a pulse frequency which is equivalent to 75% of the maximum pulse frequency (maximum heart rate). The user of an age can keep continuously taking exercise at an even pace for a long time without feeling fatigued, the exercise which raises a pulse frequency of the user to 75% of the maximum pulse frequency (maximum heart rate) decided for the age. Therefore, a pulse frequency or a heart rate at which the user can keep taking exercise at an even pace for a long time is defined as the reference evaluation value of staying power, which is calculated from $(220 - age) \times 0.75$ (hereinafter, referred to as "75% HR max"). According to another view, at a pulse frequency or a heart rate falling within a range of from 60% to 80% of the maximum pulse frequency (the maximum heart rate), an exerciser can continue exercise at an even pace for a long time. Therefore, 60% HR max to 80% HR max may be also used as the reference evaluation value of staying power.

A predictive running speed register 9h stores an estimated running speed which is calculated from the linear equation (a regression straight line), $y = ax + b$, the constants a and b of which are stored in the regression straight line register 9f, by substituting the reference evaluation value of the staying power (a pulse frequency) stored in the staying-power evaluation reference register 9g. A predictive goal time register 9i stores an estimated goal time which is obtained by dividing a distance data, which is stored as data of exercise quantity in a running distance register 9k to be described later, by the estimated running speed stored in the predictive running speed register 9h. A trial running distance register 9j stores input distance data for a trial running. The distance data for a trial running is incremented by +1 in the goal time preparation mode every time the distance input key K2 is operated. The running distance register 9k stores running distance data as data of exercise quantity. The running distance data is used for predicting how much of time a runner shall take for running the running distance. The running distance data is incremented by +1 in the goal time display mode every time the distance input key K2 is operated.

Operation of the embodiment of the invention with the structure mentioned above will be described hereafter. When the time calculating mode is set by operation of the mode selecting switch SW3, the current time data stored in the time register 9b is updated and displayed on the display unit 13 every time the time-calculating signal is input from the dividing/timing circuit 15. In the time calculating mode, the control unit 7 waits for a key input signal to be sent from the input key unit 10.

Figure 4:
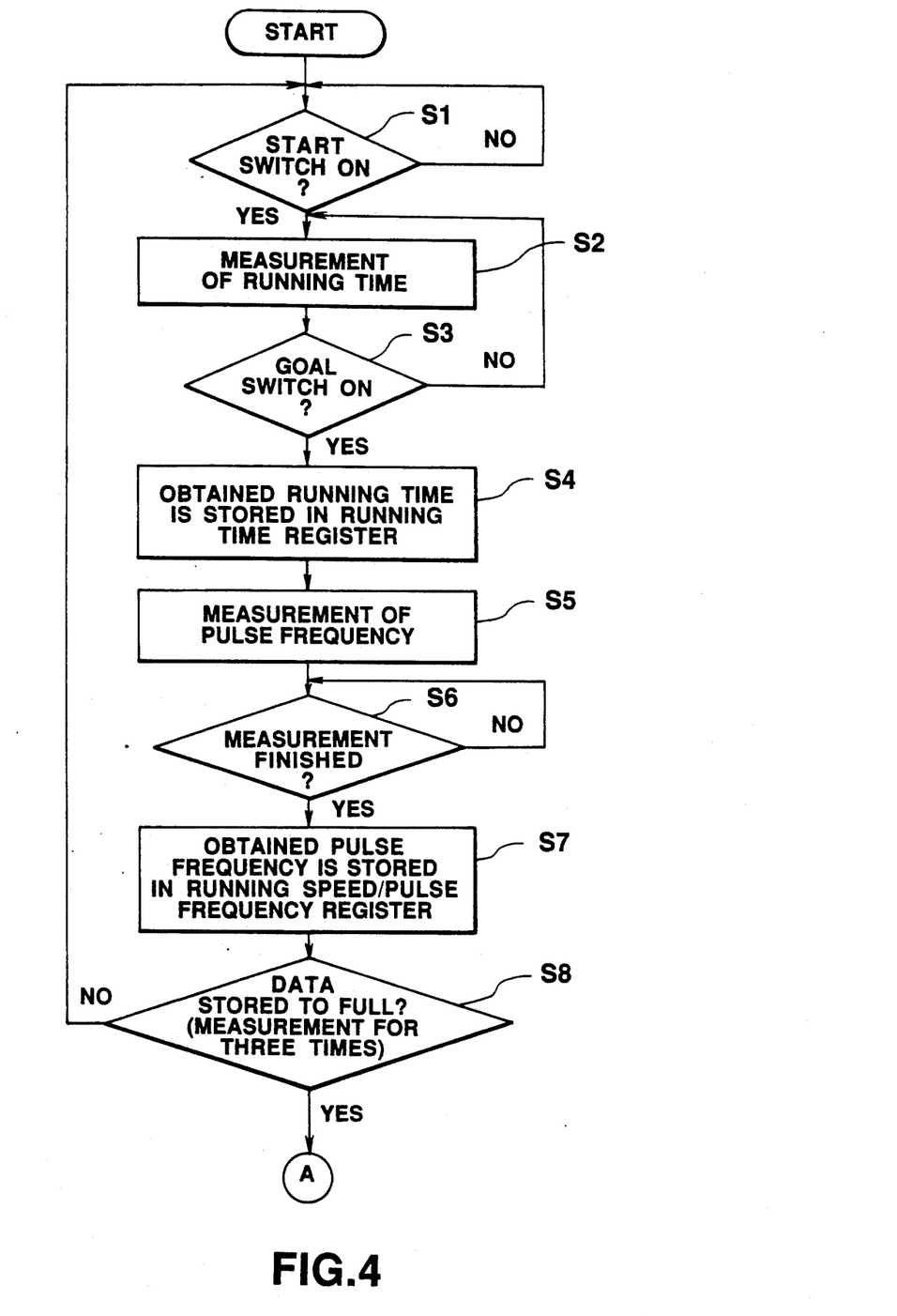
FIG. 4 is a flow chart of a part of operation of the embodiment in a goal-time preparation mode.
Figure 5:
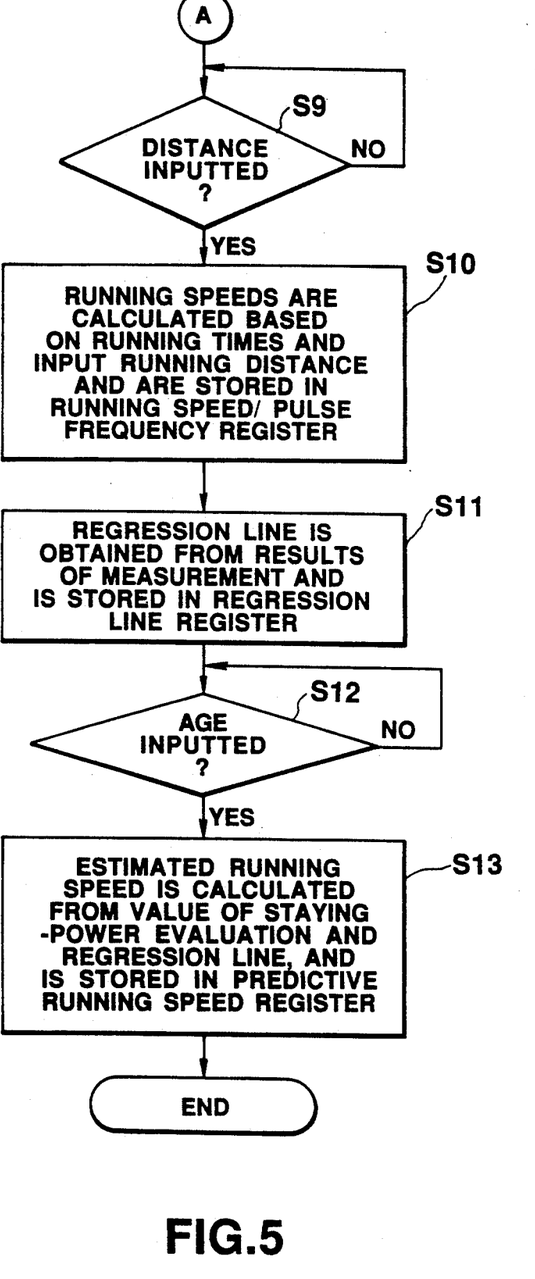
FIG. 5 is a flow chart to be connected to the flow chart of FIG. 4.

When the mode selecting switch SW3 is operated in the time calculating mode, the operation mode is switched to the goal time preparation mode, in which processes in the goal time preparation mode are performed in accordance with the flow charts of FIGS. 4 and 5. Before a runner starts operation in the goal time preparation mode, the runner selects a relatively short running course for a trial running, a distance (from a start point to a goal point) of which is known (for example, 120 m). At first, the runner makes a trial running at a relatively slow and even pace. The runner operates the start switch SW1 at a starting point and at the time he (or she) starts the first trial running.

Then, it is determined at step S1 of the flow chart of FIG. 4 that the start switch SW 1 has been operated. The operation goes to step S2, where a running-time calculating process is executed, wherein time data is counted by the time counting register 9d. It is judged at step S3 whether the goal switch SW2 is operated. The processes at steps S2 and S3 are repeatedly executed until the goal switch SW2 is operated. Meanwhile, the runner keeps running towards the goal point, and the running-time process is repeatedly executed to count up time data of the running time register 9d, thereby a running time is counted. When the runner operates the goal switch SW2 at the time he has reached the goal point, the counted running time is registered and held in the memory area of the running time register 9d for the first trial running at step S4.

At step S5, a pulse frequency calculating process is executed. In the pulse frequency calculating process, the runner puts his finger on the pulse frequency detecting unit 4 immediately after he has reached the goal point, and then the pulse frequency detecting circuit 11 detects pulses using the light emitting element 5 and the light receiving element 6, and outputs pulse signals to the control unit 7. The control unit 7 counts a time interval between successive pulse signals, i.e., measures a period of pulses to count the number of pulses per minute (a pulse frequency). Therefore, it only requires a time corresponding to one period of pulses to count the number of the pulses per minute at that time. The time required for calculating pulses varies depending on measurement conditions and physical conditions of the runner (or a user). At step S6, it is judged whether the pulse frequency calculating process has been finished. The judging process of step S6 is repeatedly executed until it is determined that the pulse frequency calculating process has been finished. When it is determined that the pulse frequency calculating process has been finished, the operation goes to the following step S7, where counted pulse frequency is stored in the pulse frequency area of the running speed/pulse frequency register 9e.

The state of the pulse frequency area is examined at step S8 to judge whether data have been stored in the area to the full. In other words, it is judged whether running speed measurement and pulse frequency measurement have been performed for three times. When the result of the judgement is "NO", then the operation returns to step S1, where the control unit 7 waits for operation of the start switch SW1 again. Meanwhile, the runner takes a rest until his pulse frequency returns to a normal pulse frequency after he finished the first trial, and then the runner starts the second trial running at a normal pace. At the second trial running, the runner operates the start switch SW1 at the start point. The judging processes at steps S1 to S8 will be executed in a similar manner described with respect to the first trial running. In the running time register 9d is stored a running time of the second trail running, and in the running speed/pulse frequency register 9e is stored a pulse frequency of the runner after his second trial running.

Similarly, finishing the second trial running and the pulse measurement, the runner starts the third trial running at a higher pace. The runner operates the start switch SW1 at the start point. After the third trial running, a running time of the third trail running is stored in the running time register 9d and a pulse frequency of the runner after the third trial running is stored in the running speed/pulse frequency register 9e. As described above, the judging processes at steps S1 to S8 will be executed until it is determined at step S8 that the running speed measurement and the pulse frequency measurement have been performed for three times, and three running times of the first to third trail running will be stored in the running time register 9d and three pulse frequencies of the runner after the first to third trial running will be stored in the running speed/pulse frequency register 9e.

When the runner have tried the trial running for three times and the pulse measurement have been performed for three times, i.e., when three running times and three pulse frequencies have been obtained as described above, the operation goes from step S8 of FIG. 4 to step S9 of the flow chart shown in FIG. 5. At step S9, it is judged whether a running distance is input. Since the running distance from the start point to the goal point is known, the running distance (for example, 120 m) is set and stored in the trial running distance register 9j of the RAM 9 by operation of the distance input key K2. When the distance has been set in the trial running distance register 9j of the RAM 9, the operation goes to step S10, where running speeds of the first to third trial running are calculated using the input running distance and the running times stored in the running time register 9d, and the calculated running speeds of the first to third trail running are stored in the running speed area of the running speed/pulse frequency register 9e. At the processes at steps S10 and S7, the running speeds and pulse frequencies for the first trial to third trail running are stored in combination in the respective areas 1, 2 and 3 of the running speed/pulse frequency register 9e.

Figure 7:
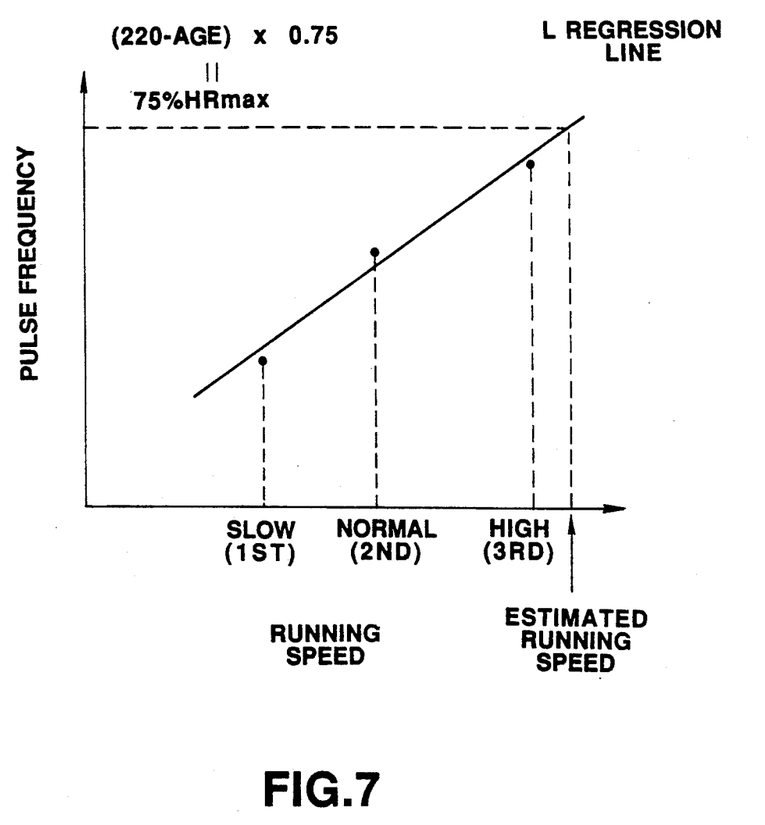
FIG. 7 is a view showing a graph illustrating contents of process executed at step S11 of the flow chart of FIG. 5.

At step S11, a regression straight line is obtained from data stored in the running speed/pulse frequency register 9e, and is stored in the regression straight line register 9f. FIG. 7 is a view illustrating the contents of the process at step 11. The y axis of an x-y coordinate is the pulse frequency and the x axis is the running speed. In the x-y coordinate, running speeds and pulse frequencies of the first trial running (at a relatively slow pace), the second trial running (at a normal pace) and the third trail running (at a higher pace), which are stored in the running speed/pulse frequency register 9e, are substituted for x and y of the linear equation $y=ax+b$, respectively, and values of the constants a and b are calculated. The calculated values of the constants a and b are stored in the regression straight line register 9f.

At the following step S12, it is judged whether age data is input by operation of the age input key K1. When age data is input, an estimated running speed is calculated from the reference evaluation value of staying power, the regression straight line: $y=ax+b$ and the constants a and b. The calculated estimated running speed is stored in the predictive running speed register 9h at step S13. The above reference evaluation value of staying power (75% HR max) is obtained from an equation: 75% HR max$=(220-$age$)\times0.75$. As shown in FIG. 7, the estimated running speed can be obtained as a value on the x axis, which value corresponds to the reference evaluation value of staying power (a pulse frequency) on the regression straight line L. Therefore, the estimated running speed can be obtained as a value x from the equation $y=ax+b$, by substituting the reference evaluation value of staying power 75% HR max for a value y. At step S12, the obtained value x, i.e., the estimated running speed is stored in the predictive running speed register 9h.

In an experiment to be described later with reference to FIG. 8, a runner is 31 years of age, and therefore the reference evaluation value of staying power is obtained as follows:

---

Reference value = $(220 - $ age$) \times 0.75$
= $189 \times 0.75$
= $141.75$

---

At the three trial running of 120 m, the following data were obtained:

|  | running time (seconds) | pulse frequency |
| --- | --- | --- |
| slow pace | 55.64 | 103 |
| high pace | 51.42 | 108 |
| higher pace | 33.18 | 144 |

From these data, the constants a and b are obtained as a=0.469 and b=42.3.
Then, the regression line is given by $$y = 0.469x + 42.3$$

Therefore, if a value 141.75 is substituted for the reference evaluation value of staying power of the regression equation, $$141.75 = 0.469x + 42.3$$
$$x = 212.0469$$
$$\approx 212 \text{ (m/minute)}$$

In this way, the estimated running speed "212" m/minute is obtained, and is stored in the predictive running speed register 9h. Now, the operation is finished.

Preparation operation has been described for predicting a running time. Hereafter, operation in the goal time display mode will be described.

Figure 6:
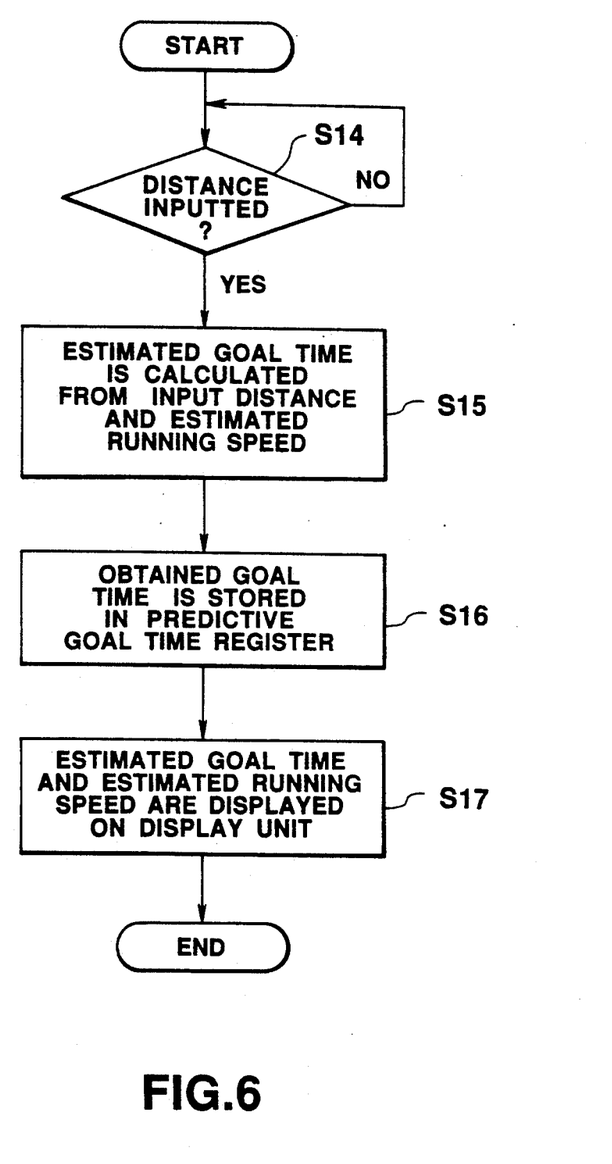
FIG. 6 is a flow chart showing operation of the embodiment in a goal-time display mode.

When the operation mode is switched to the goal time display mode by operation of the mode selecting switch SW3, it is judged at step S14 whether a distance where a runner will run is input by operation of the distance input key K2. The input distance is stored in the running distance register 9k of the RAM 9. When the distance is input, an estimated goal time is calculated from the distance stored in the running distance register 9k and the estimated running speed. The estimated goal time is obtained by dividing the distance by the estimated running speed. When the distance is set to the distance (42.195 Km) of the marathon race as in an experiment to be described later, since the estimated running speed is 212 m/minute, we obtain a goal time as follows:

$$\text{Goal time} = 42.195 \text{ Km}/212 \text{ m/minute}$$
$$= 199.033 \text{ minutes}$$
$$= 3 \text{ hours and } 19 \text{ minutes } 2 \text{ seconds}$$

The obtained goal time is stored in the predictive goal time register 9i at step S16, and the goal time and the estimated running speed stored in the predictive running speed register 9h are displayed together on the display unit 13 at step S17. The runner confirm the estimated goal time displayed on the display unit 13, and can tell how much of time he has to consume to run the whole distance of the marathon race, even though he does not actually run the whole distance, 42.195 Km. In addition, he can recognize how much of staying power he has from the calculated estimated goal time.

The results of the experiment (trial running) performed under the above mentioned conditions are as follows:

Runner: 31 years of age, male, a civil runner
Date of the trial running: November, 1991, 6:00 PM
Measuring Instruments: Treadmill (Nihon Koden Co. made), Heart rate monitor (Polar Co. made), Heartbeat recorder (Casio Computer Co. made)
Date of running: Nov. 24, 1991, 11:00 AM. Tsukuba Marathon Race.

Figure 8:
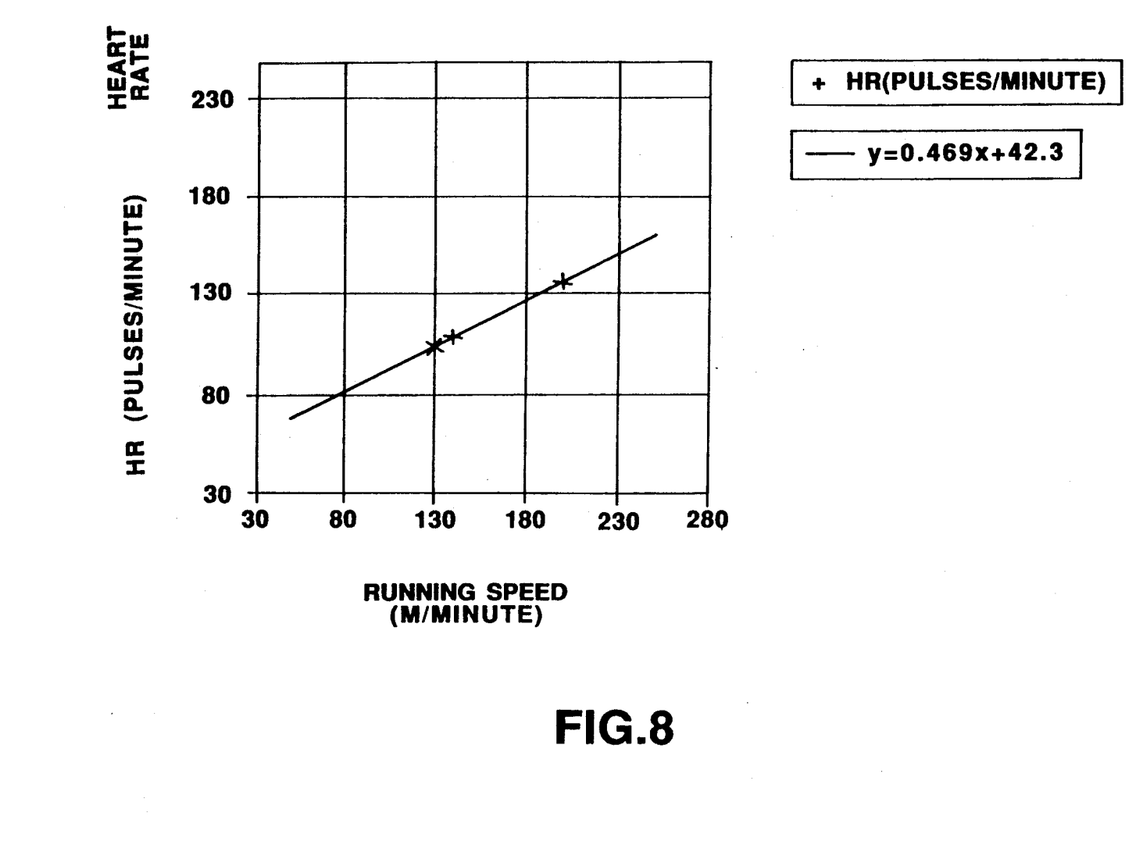
FIG. 8 is a view showing a graph illustrating measured values and a regression straight line obtained in an experiment which is performed in a similar manner to the embodiment.

FIG. 8 is a view showing a graph in which coordinates (running speed, pulse frequency at the trial running in November, 1993) are plotted with a sign "+". A regression line is given by a linear equation $$y = 0.469x + 42.3$$

Further, we have obtained the reference value and the estimated running speed shown below:

$$\text{Reference value} = (220 - 31) \times 0.75$$
$$= 141.75$$

75% HR max (estimated running speed)=212 m/minute.

The estimated goal time for the distance 42.195 Km will be 3 hours and 19 minutes 2 seconds.

The results of the marathon race on Nov. 24, 1991 are shown below:

The goal time was 2 hours and 52 minute 3 seconds.
The calculated running speed was 245 m/minute.

Comparison of the results of the marathon race with the results of the experiment (trial running) will make it clear that calculation of the estimated goal time as described in the embodiment has given a good estimation of the goal time.

The time calculating device of the present invention is applied to an electronic wrist watch in the above embodiment, but the time calculating device may be incorporated with another electronic apparatus.

In the above embodiment, an estimated running speed and an estimated running time are calculated based on pulse frequencies of the user (the runner), which are counted when the user makes trial runs for several times at different paces. The estimated running speed and the estimated running time, however, may be calculated based on data of a living body such as a maximum intake quantity of oxygen and an accumulated quantity of lactic acid in the blood of the runner, which are counted when the runner makes trial runs for several times at different paces.

In the above embodiment, the time calculating device according to the present invention has been described, which is used by the runner when the runner runs the whole distance 42.195 Km of the marathon race, but the time calculating device may be used for races of different distances or for another athletic sports such as a walking race.

Further, the time calculating device may be used not only for athletic sports but also for another races such as a swim race, a bicycle race, a ski race and so on.

Furthermore in the above embodiment, the estimated running speed and the estimated goal time are displayed on the display unit 13. But these estimated running speed and estimated goal time may be printed out on a piece of paper or may be audibly outputted through a voice composing device.

In the time calculating device of the invention, a time lapsed after a start time of a race may be subtracted from the estimated goal time of the race to count a time left before the estimated goal time will lapse. Therefore, during the marathon race the runner may confirm on the display unit 13 of the device the counted time left before the estimated goal time.

Embodiments of the present invention have been described in detail but these embodiments are simply illustrative and not restrictive. The present invention may be modified in various manners. All the modifications and applications of the present invention will be within the scope and spirit of the invention, so that the scope of the present invention should be determined only by what is recited in the present appended claims and their equivalents.

What is claimed is:

1. A time calculating device comprising:
   measuring means for measuring data of a living body of a user when the user takes exercise at least twice at different paces;
   input means for inputting data of exercise quantity;
   storing means for storing data of exercise quantity inputted by said input means;
   calculating means for calculating, based on the data of a living body measured by said measuring means, an estimated time required for finishing exercise quantity expressed by the data of exercise quantity stored in said storing means; and
   output means for outputting the estimated time calculated by said calculating means.

2. A time calculating device according to claim 1, wherein said measuring means comprises pulse frequency calculating means which counts pulse frequencies of the user, when the user runs a predetermined distance at least twice at different paces.

3. A time calculating device according to claim 2, wherein said pulse frequency calculating means comprises a light emitting element and a light receiving element.

4. A time calculating device according to claim 1, wherein said output means comprises display means for displaying the estimated time calculated by said calculating means.

5. A time calculating device according to claim 1, wherein said calculating means comprises:
   first calculating means for calculating exercise hardness based on data of a living body of the user measured by said measuring means; and
   second calculating means for calculating an estimated time required for finishing, at the exercise hardness calculated by said first calculating means, exercise quantity expressed by the data of exercise quantity stored in said storing means.

6. A time calculating device comprising:
   measuring means for obtaining heart rates of a user when the user runs at different paces;
   input means for inputting distance data;
   storing means for storing distance data inputted by said input means;
   calculating means for calculating, based on the heart rates obtained by said measuring means, a time which the user will consume to run a distance expressed by the distance data stored in said storing means; and
   output means for outputting the time calculated by said calculating means.

7. A time calculating device according to claim 6, wherein said measuring means comprises a light emitting element and a light receiving element.

8. A time calculating device according to claim 6, wherein said calculating means comprises:
   first calculating means for calculating exercise hardness based on heart rates of the user obtained by said measuring means; and
   second calculating means for calculating a time which the user will consume to runs, at a pace expressed in terms of the exercise hardness calculated by said first calculating means, a distance expressed by the distance data stored in said storing means.

9. A time calculating device comprising:
   first storing means for storing heart rate data and speed data of a user obtained when the user runs at different paces;
   first calculating means for calculating constants of a regression line based on heart rate data and speed data stored in said first storing means;
   second storing means for storing distance data;
   second calculating means for calculating speed data expressed in terms of predetermined exercise hardness, based on the constants of the regression line calculated by said first calculating means;
   third calculating means for obtaining time data by dividing distance data stored in said second storing means by speed data calculated by said second calculating means; and
   displaying means for displaying time data obtained by said third calculating means.

10. A time calculating device according to claim 9, further comprising:
    input means for inputting distance data;
    time calculating means for calculating a running time;
    speed calculating means for calculating speed data to be stored in said first storing means from distance data inputted by said input means and the running time measured by said time calculating means.

11. A time calculating device according to claim 9, wherein said constants of the regression line are constants a and b of an equation of $y = ax + b$, where y is expressed by pulse frequency data and x is expressed by speed data.

12. A time calculating device according to claim 9, further comprising age data storing means for storing age data, and wherein said second calculating means calculates running speed data expressed in terms of exercise hardness, the running speed data which expresses a running speed at which the user runs and will have a heart rate corresponding to a predetermined percentage of the maximum heart rate determined for the age data stored in said age data storing means.

13. A time calculating device according to claim 12, wherein said heart rate corresponding to the predetermined percentage of the maximum heart rate falls within a range of from 60% to 80% of the maximum heart rate.

14. A time calculating device according to claim 9, further comprising distance data input means for inputting distance data to be stored in said second storing means.

15. A time calculating device according to claim 9, further comprising pulse sensing means for obtaining heart rate data to be stored in said first storing means.

16. A time calculating device according to claim 15, wherein said pulse sensing means comprises a light emitting element and a light receiving element.

17. A time calculating device according to claim 9, wherein said time calculating device is incorporated in a casing of a wrist watch.

* * * * *